United States Patent [19]
Nanba

[11] Patent Number: 5,773,426
[45] Date of Patent: Jun. 30, 1998

[54] PROTEOGLUCAN AND ANTIDIABETIC DRUG THEREOF

[75] Inventor: Hiroaki Nanba, Amagasaki, Japan

[73] Assignee: Masaki Shirota, Paramus, N.J.

[21] Appl. No.: 660,405

[22] Filed: Jun. 7, 1996

[51] Int. Cl.$^6$ .................. A61K 31/715; A61K 35/78; C07K 4/10

[52] U.S. Cl. .................. 514/54; 424/195.1; 514/8; 514/866; 530/395; 536/123.1; 536/123.12

[58] Field of Search .................. 514/54, 8, 866; 424/195.1; 536/123.1, 123.12; 530/395

[56] References Cited

FOREIGN PATENT DOCUMENTS 63-56881  11/1988  Japan.
6-312936  11/1994  Japan.

OTHER PUBLICATIONS

Yoshida et al. *Nippon Shokuhin Kagaku Kogaku Kaishi*, vol. 43 No. 6, pp. 748–755, (1996).

Keiko Kubo et al., "Anti–diabetic Activity Present in the Fruit Body of *Grifola frondosa* (Maitake).I,"Biol.Pharm..Bull., 17(8): 1106–1110(1994).

Masashi Tomoda et al., "Glycan Structures of Ganoderans B and C, Hypoglycemic Glyacans of *Ganoderma Lucidum* Fruit Bodies*," Phytochemistry, 25(12): 2817–2820 (1986).

*Primary Examiner*—John Kight
*Assistant Examiner*—Howard C. Lee
*Attorney, Agent, or Firm*—Morgan, Lewis & Bockius LLP

[57] ABSTRACT

This Invention is to provide a proteoglucan and an antidiabetes drug containing the proteoglucan, as an active ingredient, which possess an excellent effect against non-insulin dependent diabetes mellitus. The proteoglucan under this Invention has β-1,6 main chain with α-1,4 branched, with the average molecular weight of $2 \times 10^5$, acting positive both in anthrone-sulfuric acid method and Lowry's method, having the chemical structure as indicated in the following general formula.

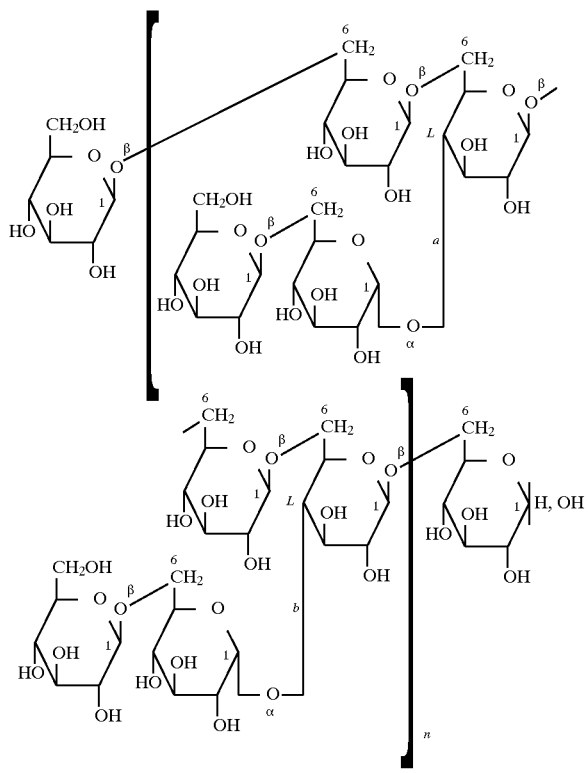

The above proteoglucan is obtained easily through the hot-water extraction from fruit body and/or mycellium of Maitake and/or Chorei Maitake. This proteoglucan has an activity to ameliorate the glucose transport and bioavailability at myocardium, skeltal muscles and fat tissue cells, etc. of the patient with non-insulin dependent diabetes mellitus, and is very useful as a pharmaceutical composition to treat and/or prevent from non-insulin dependent diabetes mellitus.

4 Claims, No Drawings

PROTEOGLUCAN AND ANTIDIABETIC DRUG THEREOF

BACKGROUND OF THE INVENTION

1. Field of the Invention

This Invention is related to the proteoglucan which has the ability to ameliorate hyperglycemia, and the antidiabetes drug which contains the proteoglucan as an active ingredient. The material and the drug covered in this Invention is effective for the treatment and prevention of diabetes, especially against non-insulin dependent diabetes mellitus (hereinafter "NIDDM"), and can be applied in oral administration.

2. Description of the Prior Art

Many people suffer from diabetes, especially NIDDM, and a number of drugs are available to improve the conditions of the particular disease. Sulfonyl urea derivatives are known as one type of these drugs. They stimulate β-cells of Langerhans's islands in pancreas to promote secretion of insulin.

However, above treatment has a problem that, although insulin may be replenished for a while, the pancreas would decline gradually and the secretion of insulin decreases.

Another type of drug, such as biguanide derivatives, is also offered. However, these drugs are known to produce anaerobic metabolism in the course of glucose consumption, thus causing lactic acidosis as a side effect.

Also, some drugs are presented aiming for the prevention of sucrase activity. However, by taking these drugs, the glucose which is an essential nutrient for human body would pass through the digestive system without absorbed. Even though the elevation of blood glucose may be inhibited to some extent, the supply of glucose to cell tissues of human body would be decreased and the cell tissues would have to consume their own proteins. At the same time, the dissolution of fat tissues would be accelerated resulting in the elevation of liberated plasma fatty acid.

In the meantime, insulin is essential in the treatment of diabetes, especially for insulin-dependent diabetes mellitus (hereinafter "IDDM"). In this case, however, insulin has to be administered by injection and very careful attention is required in the administration in terms of its timing and dosage. It is preferable, therefore, for the patients with NIDDM who are able to secrete insulin to some degree, that the drug by oral administration would be developed and offered.

Recently, it is considered that the cause of NIDDM is due to the malfunction of glucose transport at peripheral tissues especially at myocardium, skeltal muscles and fat tissue cells which are major glucose consuming cells (hereinafter "Target Cells"). As a drug to improve glucose transport, thiazolidine derivatives such as 5-[4-(1-Methylcyclohexylmethoxy) benzyl] thiazolidine-2,4-dione was presented: but it has not been marketable since the possibility of causing a cataract was pointed out.

SUMMARY OF THE INVENTION

[Object of the Invention]

Under the circumstances, this Invention has the object to present a proteoglucan and an antidiabetic drug containing the glucan thereof as an active ingredient which has an ability to improve the glucose trasport and the bioavailability at the Target Cells of patients with NIDDM with less side effect.

[Characteristics of the Invention]

The Inventor has extensively searched for the sources to achieve the above object from the materials of foods and crude drugs that have been safely taken in the past.

It is known that Ginseng Radix, Coicis Semen or Coix seed, etc. have been used as crude drugs for the treatment of diabetes. Also, it is reported that mycelium or fuit body of Basidiomycetes, such as Ganoderma lucidum, contains active agents to lower blood glucose.

The Inventor examined active agents from the fruit body of various Basidiomycetes since some of them have been legendary appreciated as medicines. As a result, the Inventor has accomplished this Invention after he found that an agent extracted from Maitake has an activity to lower the blood glucose which would contribute to improve the glucose transport and bioavailability at the Target Cells of patients with NIDDM.

Maitake has been taken as a culinary mushroom for a long time and no side effects have been reported. Therefore, this Invention has made it possible to offer the effects of treatment and prevention against NIDDM.

A proteoglucan, the first invention, as indicated in the general formula below in its glucan part, has β-1,6 main chain with α-1,4 branched, with the average molecular weight of $2 \times 10^5$, acting positive both in anthrone-sulfric acid method and Lowry's method.

The general formula of the glucan part of the proteoglucan is:

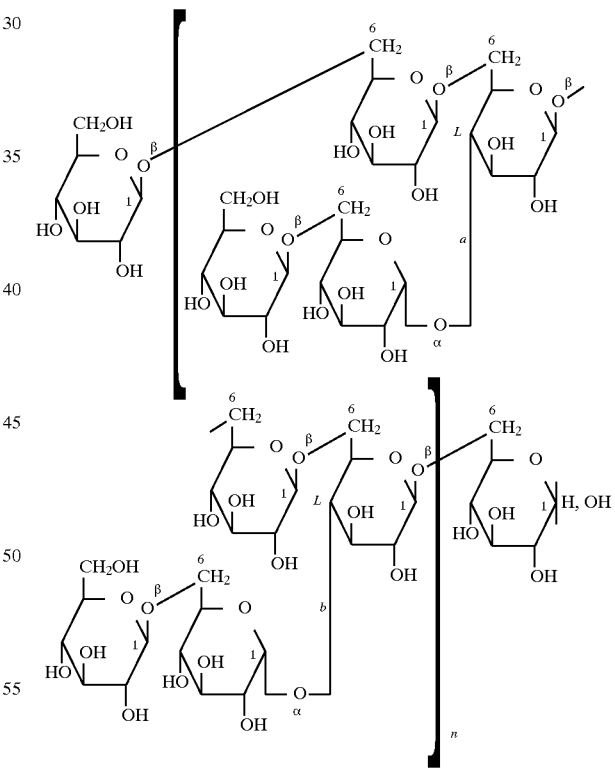

The numbers in the formula indicate the position. a and b represent branches which positions can be exchanged. n is an integral number between 100–200.

A proteoglucan, the second invention, is obtained through hot-water extraction from Maitake (*Polyporus frondosus*) and/or Chorei Maitake (*Polyporus umbellatus*). The temperature of the hot water is properly selected considering the extraction efficiency and extraction time, etc. Usually it is not less than 60° C., preferably 80°–200° C.

It is even more preferable if the temperature of 80°–150° C. or 100°–150° C. are employed. It is possible, however, to use the temperature of 40°–60° C. if the extraction time is long enough.

An antidiabetes drug, the third invention, contains the proteoglucan as indicated in the general formula below in its glucan part, has β-1,6 main chain with α-1,4 branched, with the average molecular weight of 2×10$^5$, acting positive both in anthrone-sulfuric acid method and Lowry's method.

The general formula of the glucan part of the proteoglucan is:

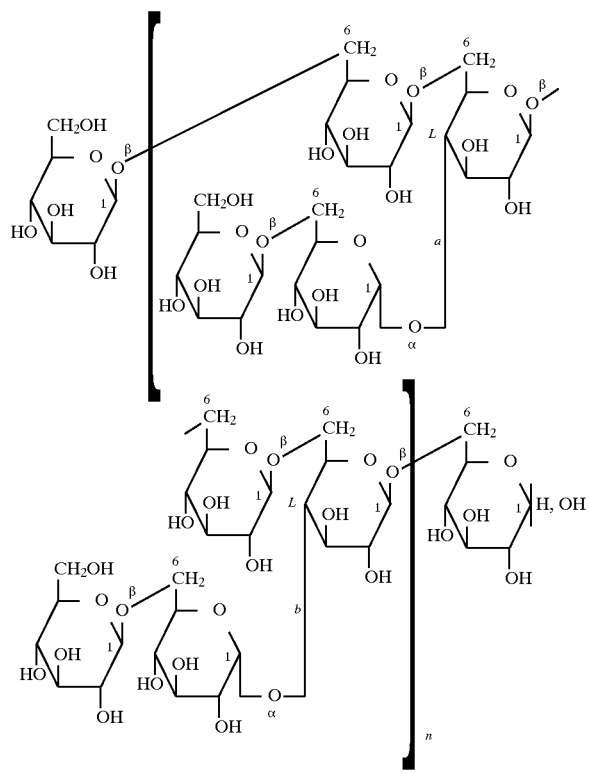

The numbers in the formula indicate the positions. a and b represent branches which positions can be exchanged. n is an integral number between 100–200.

A proteoglucan, contained in the antidiabetes drug as an active agent, the fourth invention, is obtained through the hot-water extraction from Maitake and/or Chorei Maitake. As for the temperature of the hot water, the similar temperatures are applied to those indicated in the aforementioned second invention.

The drugs as described in the third and fourth invention above are very effective for the treatment and prevention of non-insulin dependent type diabetes mellitus (NIDDM).

[Effect of the Invention]

The proteoglucan with the structure as indicated in Example 3 hereof has an excellent activity to lower blood glucose. Also, it does not stimulate or enhance the insulin secretion like the sulfonyl urea derivatives that have been offered as antidiabetes drugs. Further, as indicated in Example 4 hereof, this proteoglucan has an ability to ameliorate glucose transport or bioavailability at major glucose consuming cells, i.e. the Target Cells such as myocardium, skeltal muscles, fat tissue cells, etc.

Therefore, by using this proteoglucan or the antidiabetes drug based on this glucan as an active agent, the conditions of hyperglycemia would be ameliorated due to the release or prevention of insulin resistance at the Target Cells. It could give the proteoglucan or the antidiabetes drug thereof a possibility to be widely used as a basic drug for the treatment and prevention of diabetes.

The proteoglucan in the second invention and the proteoglucan contained in the antidiabetes drug in the fourth invention can be located in the fruit body and/or mycellium of Maitake (*Grifola frondosus*) and/or Chorei Maitake (*Grifola umbellatus*), and easily obtained through the hot-water extraction.

DETAILED DESCRIPTION OF THE INVENTION

The proteoglucan in this Invention is obtained by the method as described in Example 1 below in the hot-water treatment of fruit body and/or mycellium of Maitake which belongs to the Polyporaceae family. Further, the chemical structure is identified under the method as described in Example 2 below. The identified agent is called as the "Proteoglucan" hereinafter.

The Proteoglucan in the first invention and the Proteoglucan contained in the antidiabetes drug as an active agent in the third invention are not limited to those extracted by the hot-water from Maitake and/or Chorei Maitake as indicated in the second and the fourth inventions. Any agent that has a formulation as indicated in the aforesaid chemical structure will be applied.

The antidiabetes drug under this invention contains the Proteoglucan with the identified structure as an active agent, where the Proteoglucan can be used as it is, in a solid form, in a diluted liquid form, or combined with excipients. The form of the antidiabetes drug and that of the administration thereof can be in a liquid, paste or solid form which is normally taken orally by way of pulveres, tablets, granulated powder, capsules, syrups, emulsions, etc. It can be also developed in the form of sublingual tablets and suppositories. Further, it may be administered by injection. As a dosage, the Proteoglucan in the amount of 1–100 mg/day, normally 5–50 mg/day (or 5–10 mg/day) is used by way of oral administration or others. This is an appropriate dose to demonstrate its effectiveness.

The specific samples to use as diluents and excipients are; lactose, starch, dextrin, calcium phosphate, calcium cabonate, magnesium oxide, magnesium stearate, sodium bicarbonate, aluminium silicate, aluminium hydroxide, dried yeast, water, milk, etc.

Also, dried fruit body powder of Maitake and/or Chorei Maitake, its solid form or extracted liquid form, that contain the Proteoglucan, may be used as health foods or as dietary supplements with the dosage where the amount of contained Proteoglucan is not sufficient enough to demonstrate the pharmaceutical curing effect but enough to maintain good health. In this case, the preferable forms would be tablets, granulated powder, soft capsules, liquid, tea, etc.

EXAMPLES

The Invention is further explained by referring to the examples and experiments as hereunder;

Example 1

The method of obtaining the Proteoglucan in this Invention is described in (1) and (2) below.

(1) Fruit body of Maitake is dried and pulverized. The powder 1 kg was added by 10 litters of distilled water and treated by an autoclave with 1.2 atoms at 120° C. for 30 minutes. After cooled off and centrifuged, the supernatant was collected. The supernatant was mixed with the same amount of ethanol and left at 4° C. for 12 hours. Then the float material was centrifuged at 8000 rpm for 15 minutes to collect the agent.

(2) The material collected above was solved in water and chromatographed on DEAE-Sepharose CL-6B column (2.5 cm$\phi$×62 cm) and only anthrone-sulfuric acid test positive fraction was collected from passed-through fraction.

After dialyzed and desalted, this fraction was concentrated under reduced pressure at low temperature.

This concentrated liquid was put on Sepharose CL-4B column (3 cm$\phi$×98 cm) and eluted by distilled water, and anthrone-sulfuric acid test positive fraction was collected.

The Proteoglucan was obtained after dialyzed and concentrated the fraction under reduced pressure at low temperature.

Example 2

The sample material obtained in above Example 1 was analyzed to examine its characteristics and to identify its general formula.

(1) This material was positive for both anthrone-sulfuric acid method and Lowry's method, and the ratio of sugar and protein is 20.6:1.

(2) Optical Activity

Specific rotation $[\alpha]_D$=+98.04 (c=0.15, $H_2O$, 15° C.)

(3) Molecular Weight

Molecular weight was measured by molecular sieve gel chromatography.

$M.W.$=(1.9–2.0)×$10^5$

Sedimentation velocity was measured by HITACHI 282 ultracentrifuge (with RA-60H rotor, single cell), and the following sedimentation constant was obtained;

S(10.4° C., W)=17.4

(4) Species of the Glucose Constituent 1 mg of the sample material was methanolyzed in 1 ml of a 5% HCl/methanol solution at 100° C. for 6 hours in a sealed tube. The product of this reaction was repeatedly dried under concentrated reduced pressure to completely remove HCl, and then analyzed by gas liquied chromatography using SE-20 (silicon-gum GE) with acetonitrile as a solvent. The chromatography gave only glucose.

These results from above (1) and (4) indicate that this material is a proteoglucan.

(5) 1 mg of the sample material was dissolved in McIlvain buffer (0.1 M, pH 7.0) and each mixture was added by 0.1 mg each of the following enzymes ①~③ to allow them to stand for one hour at 52° C.

① endo-β-glucosidase
② endo-α-glucosidase
③ exo-βglucosidase, and then exo-α-glucosidase The amount of the produced glucose was measured by glucose-oxidase method. The results are indicated in Table 1 hereunder.

TABLE 1

| No. | Provided Enzyme | Liberated glucose (mg) |
|---|---|---|
| 1 | endo-β-glucosidase | 0.23 |
| 2 | endo-α-glucosidase | 0.15 |
| 3 | exo-β-glucosidase →exo-α-glucosidase | 0.11 |

(6) Methylation Analysis

In order to investigate the modes of linkages of monomer units in the chained glucan, the sample material was completely methylated by Hakomori's method. The methylated product was added by 5% HCl/methanol solution and hydrolyzed at 100° C. in a sealed tube. This sample was analyzed by gas liquid chromatography using Neopentylglycol succinate column and the results were obtained as indicated in Table 2 below.

TABLE 2

| Chemical kind of detection | Molar ratiol |
|---|---|
| 2,3,4,6,-tetra-o-methy D-glucopyranoside | 1.00 |
| 2,3,4-tri-o-methyl D-glucopyranoside | 1.97 |
| 2,3-di-o-methyl D-glucopyranoside | 0.98 |

(7) Nuclear Magnetic Resonance Analysis $^{13}$C-NMR spectrum was taken on a Varian XL-200 (50.3 MHz). Sample 10 mg was dissolved in 0.8 ml of heavy water with NaOH concentration of 0.2 M and the spectrum was measured with acetonitrile as the standard to obtain the signals as shown in Table 3 below. Unit is ppm.

TABLE 3

| 100.5, | 99.2, | 78.8, | 73.9, | 72.1, | 71.0, | 70.1, | 61.1 |
|---|---|---|---|---|---|---|---|

In the above table, it is observed that 78.8 ppm belongs to 1,4-bonding and 70.1 ppm to 1,6-bonding.

(8) Chemical Structure Formula

Based on the results as mentioned above, especially those in (5) (6) and (7), it is concluded that this sample material has a general formula as previously indicated.

Example 3

Next, pharmacological effects of the Proteoglucan in this Invention are discussed.

(1) Animals in experiment

Seven week old female spontaneously diabetic mice (KK-$A^y$) purchased from Clear Japan Inc. were raised laboratory chow at 25±1° C. and 55% humidity under specific pathogen-free conditions for one week, and used in the experiments at the age of eight weeks old.

KK-$A^y$ mouse is a model animal of NIDDM. It is developed by transplanting an obesity gene $A^y$ into the KK-mouse which was reported to be spontaneously diabetic in 1962. KK-$A^y$ mice usually demonstrate obesity and hyperglycemia at the age of 4 weeks old.

(2) Sample feed and the Control feed 800 ml of the 0.025% Proteoglucan solution as obtained in Example 1 was added to 1 kg powder of CRF-1 feed purchased from Charles River Co. After thorough kneading, 3×3 cm squares were cut and dehydrated at 80° C. for 20 hours. The Proteoglucan content in the obtained experimental feed is 0.02%.

The control feed was made by adding distilled water to the CRF-1 feed, kneading and treating the same manner as above.

During the period in the laboratory and experiment, the control feed, sample feed and water were provided ad libitum.

(3) Experiments and Results

In the experiment group, the 8 week old mice were bred with the sample feed with 0.02% of the Proteoglucan in its content. Control feed continued to be fed to the mice in the control group. The blood was collected periodically from experimental mice and control mice, and glucose level (mg/dl) was measured. Averaged glucose levels in both groups are indicated in Table 4 below.

TABLE 4

| Group | Breeding time | | | | |
|---|---|---|---|---|---|
| | at start 0 day | After 7th day | After 14th day | After 21st day | After 28th day |
| Control group | 291 | 322 | 379 | 411 | 392 |
| Experiment group | 292 | 231 | 202 | 220 | 211 |

Table 4 shows that the blood-glucose in the control group continued to increase to high levels, while that in the experiment group which were bred with 0.02% Proteoglucan was clearly inhibited from blood glucose elevation.

Example 4

Eight week old female KK-A$^y$ mice (including the one week period in laboratory) were fed ad libitum with the Proteoglucan 0.02% containing feed or control feed for 14 days. No feed was given for 18 hours before 0.1 mg/ml glucose solution was orally administered in the amount of 0.2 ml per 10 g of body weight, and the glucose levels (mg/ml) were measured before administration and at 15, 30 and 60 minutes after the administration, respectively. Averaged glucose values in each group were indicated in Table 5 below.

TABLE 5

| Group | Time of measurement before administration | | | |
|---|---|---|---|---|
| | 0 min. | after 15 min. | 30 min. | 60 min. |
| Control group | 115 | 611 | 502 | 398 |
| Experiment group | 114 | 403 | 320 | 281 |

Recently, the number of NIDDM patients has increased, especially among the elderly pepole, who have almost no difference in the glucose level at the time of empty stomach but elevate the glucose level under the glucose tolerance conditions when it does not decrease smoothly. The condition of the NIDDM gets worse, as a result, since the patients have longer period with the high level of blood glucose. The results as indicated in above Table 5 suggest that the Proteoglucan has the ability to ameliorate the symptoms of diabetes.

Next, the mechanism of the activity by the Proteoglucan was examined as described in Experiment 1 and 2 hereunder.

Experiment 1

This experiment is to investigate the relationship between the plasma insulin concentration and blood glucose.

A sulfonyl urea derivative, among the antidiabetes drugs, is known to stimulate β-cells of Langerhans's islands in pancreas and promote insulin secretion, thus subsiding blood glucose by the increase of plasma insulin. Therefore, the Proteoglucan was examined to see if it has such activity or not.

In the experiment mice in Example 3, plasma insulin ($\mu$U/ml) was also measured, indicating the average values in each group in Table 6.

TABLE 6

| Group | Time of measurement | | | |
|---|---|---|---|---|
| | at start | after 7th day | after 14th day | after 21st day |
| Control group | 251 | 302 | 397 | 1610 |
| Experiment group | 252 | 240 | 301 | 352 |

By comparing the above Table 6 and Table 4 of Example 3, it is indicated that the blood glucose is lower in the experiment group which was given the Proteoglucan in the feed despite the fact that the plasma insulin concentration is low. This means that the lowering blood glucose or inhibiting blood glucose elevation is not due to the increase of plasma insulin. At least it is not contributed by the promotion of insulin secretion.

Deficiency of insulin is said to be one of the causes of diabetes. During the beginning stage of the disease, however, the plasma insulin level is rather elevated compared to that of healthy people. This would make the disease condition worse by increasing the insulin resistance at Target Cells.

Therefore, it is required to adjust the abnormal level of plasma insulin concentration. The effect of the Proteoglucan as indicated in Experiment 1 is a great advantage over the conventional blood glucose lowering drugs which do not possess this effect.

Experiment 2

Advancement of the study on NIDDM has paid more attention to the receiver side of insulin rather than the supplier side. The Inventor has examined the Proteoglucan from this particular point of view.

Eight week old female KK-A$^y$ mice were bred with the Proteoglucan 0.02% containing feed or control feed ad libitum for 14 days, then the hepatocytes were isolated. The isolated hepatocytes were cultured for 24 hours to obtain monolayer primary cultured hepatocytes which were used as target cells. Insulin was added to the target cells so as to make the final concentration 0–10$^{-4}$ $\mu$U/ml. Then $^{125}$I-insulin was added to make 7.4 KBq, and cultured at 4° C. for 18 hours respectively. After completion of the culture and thorough washing, the target cells were dissolved with 0.2 M of NaOH and the number of $^{125}$I-insulin binded with the cells were counted. The results are indicated in the following Table 7.

TABLE 7

| | $^{125}$I-insulin Binding Level (cpm) | | | | |
|---|---|---|---|---|---|
| insulin concentration ($\mu$U/ml) | 0 | 10$^{-7}$ | 10$^{-6}$ | 10$^{-5}$ | 10$^{-4}$ |
| Control group | 2.6 | 1.2 | 1.2 | 1.0 | 0.9 |
| Experiment group | 10.0 | 2.3 | 1.0 | 1.1 | 1.2 |

Recently, it is known that the glucose is transported into the cells when the insulin is binded with the insulin receptors of Target Cells. Therefore, it can be said that the insulin activity functions efficiently as long as the binding action with insulin receptors is active, even under the low concentration of plasma insulin. However, glucose transport would be difficult when high concentration of plasma insulin is required to bind with insulin receptors.

In the control-fed mice group, it is observed that the insulin binding action is low especially under the lower insulin concentration. It would create a barrier for glucose transport, remaining high glucose in the blood.

On the contraty, the insulin binding receptors were observed in the Proteoglucan-fed mice group even under the low concentration of insulin, suggesting the amelioration of diabetes. In other words, it is clearly indicated that the Proteoglucan has the activity to lower the elevated glucose conditions by releasing the insulin resistance at Target Cells.

This Invention should not be limited to the examples specifically indicated in the aforesaid Examples. It should include those that may be adjusted or modified, within the range of this Invention, depending on its object or usage.

What is claimed:

1. A Proteoglucan wherein the formula of the glucan part of said proteoglucan is:

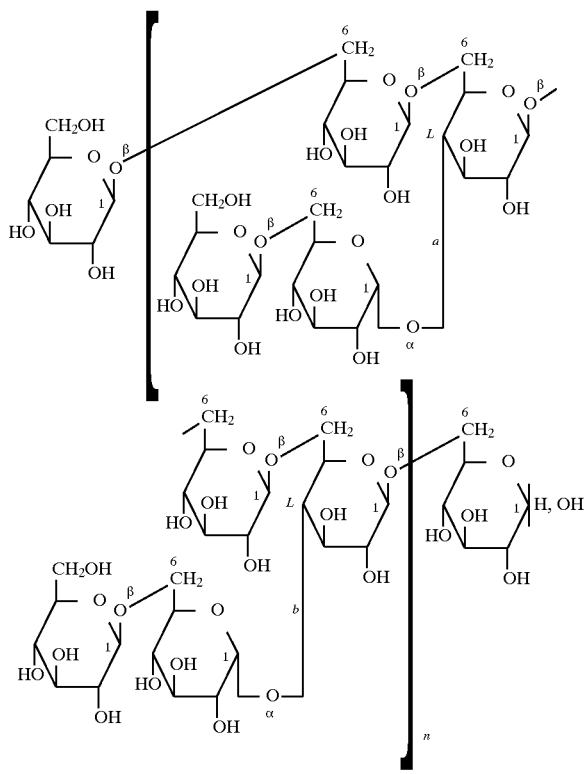

wherein n is an integral number ranging from 100 to 200 and wherein said proteoglucan has an average molecular weight of $2 \times 10^5$ and gives positive results in anthrone sulfuric acid method and Lowry's method.

2. The proteoglucan according to claim 1, obtained by (1) hot-water extraction from Maitake (*Polyporus frondosus*); Chorei Maitake (*Polyporus umbellatus*); or a mixture thereof; (2) subjecting the extraction to anthrone sulfuric acid method and Lowry's method; and (3) collecting only the fraction testing positive both in anthrone sulfuric acid method and Lowry's method.

3. An antidiabetic drug composition containing a proteoglucan as the active ingredient, wherein the formula of the glucan part of said proteoglucan is:

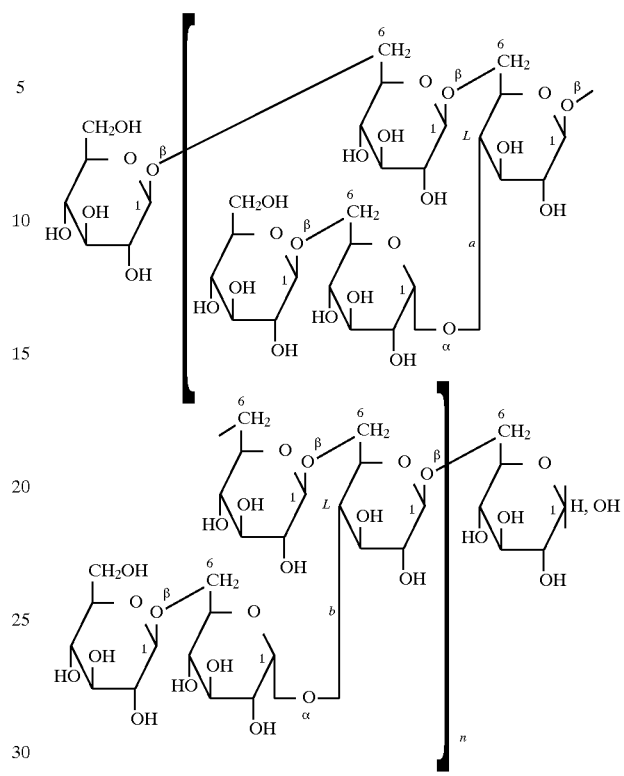

wherein n is an integral number between 100–200, wherein said proteoglucan comprises β-1,6 main chain with α-1,4 branched and has an average molecular weight of $2 \times 10^5$ and wherein said proteoglucan consists essentially of a proteoglucan acting positive in both the anthrone-sulfuric acid method and Lowry's method.

4. An antidiabetic drug composition containing a proteoglucan as the active ingredient, wherein the formula of the glucan part of said proteoglucan is:

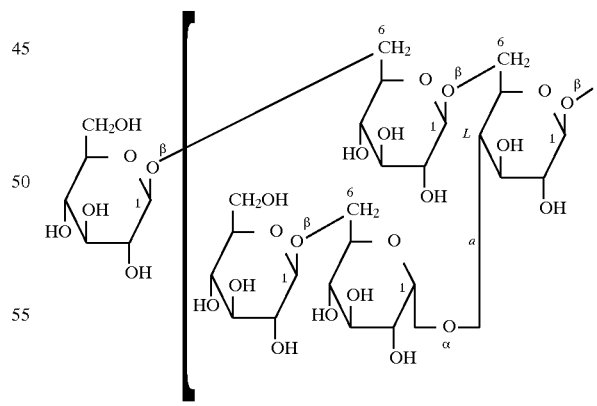

-continued

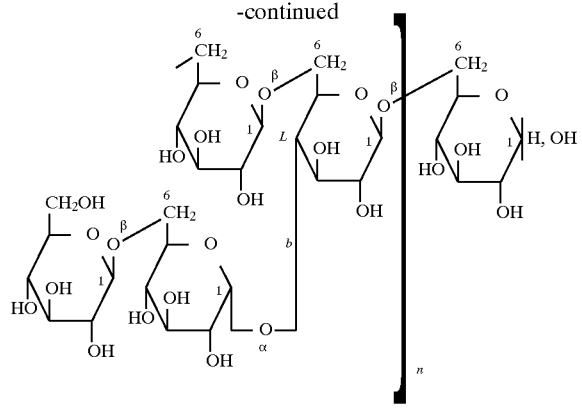

wherein n is an integral number ranging from 100 to 200 and wherein said proteoglucan has an average molecular weight of $2\times10^5$ and gives positive results in anthrone sulfuric acid method and Lowry's method, wherein said proteoglucan is obtained by (1) hot-water extraction from Maitake (*Polyporus frondosus*); Chorei Maitake (*Polyporus umbellatus*); or a mixture thereof; (2) subjecting the extraction to anthrone sulfuric acid method and Lowry's method; and (3) collecting only the fraction testing positive both in anthrone sulfuric acid method and Lowry's method.

* * * * *